United States Patent [19]

Lee

[11] Patent Number: 4,738,802
[45] Date of Patent: Apr. 19, 1988

[54] PROCESS FOR PREPARING ALKYL α-KETO-CARBOXYLIC ACIDS FROM ALKYL HALIDES

[75] Inventor: John Y. Lee, Baton Rouge, La.

[73] Assignee: Ethyl Corporation, Richmond, Va.

[21] Appl. No.: 552,281

[22] Filed: Nov. 16, 1983

Related U.S. Application Data

[63] Continuation-in-part of Ser. No. 353,473, Mar. 1, 1982, abandoned.

[51] Int. Cl.$^4$ ..................... C07C 51/10; C07C 59/185
[52] U.S. Cl. .................................. 260/413; 562/520; 562/577; 562/606
[58] Field of Search ................. 562/520, 577; 260/413

[56] References Cited

U.S. PATENT DOCUMENTS 4,152,352  5/1979  Perron ................................. 562/406

FOREIGN PATENT DOCUMENTS 2026478A  2/1980  United Kingdom .

OTHER PUBLICATIONS

March, Advanced Organic Chemistry, Reactions, Mechanisms, and Structures, 2nd editon, NY: McGraw-Hill Book Co., 1979, pp. 436–438.

Rodd, The Chemistry of Carbon Compounds, (1952 edition), vol. 1, pp. 226–229.

Primary Examiner—Vivian Garner
Attorney, Agent, or Firm—John F. Sieberth; Willard G. Montgomery; Patricia J. Hogan

[57] ABSTRACT

A process for the production of an alkyl α-keto-carboxylic acid of the general formula:

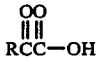

wherein: R is a linear or branched alkyl radical having from 1 to about 20 carbon atoms which comprises reacting an alkyl halide of the formula:

RX where R is as defined above and X represents halogen, in a liquid solvent medium, with carbon monoxide at elevated temperature and pressure in the presence of a catalytic amount of a metal carbonyl compound and an alkali metal inorganic base or an alkaline earth metal inorganic base. Optionally, small amounts of LiI and/or bis(1,2-diphenylphosphino)ethane may be present in the reaction as co-catalysts.

5 Claims, No Drawings

PROCESS FOR PREPARING ALKYL α-KETO-CARBOXYLIC ACIDS FROM ALKYL HALIDES

CROSS-REFERENCE TO RELATED APPLICATIONS

This is a continuation-in-part of prior co-pending application, Ser. No. 353,473, filed Mar. 1, 1982, now abandoned entitled "Process for Preparing Alkyl Alpha-Keto-Carboxylic Acids from Alkyl Halides".

BACKGROUND

The present invention relates to a process for the carbonylation of an alkyl halide to form an alkyl α-keto-carboxylic acid as the predominant product.

The practical value of such α-keto-carboxylic acids is that they can be used to prepare the corresponding α-amino-acids of α-hydroxy acids which play an important role in biochemistry.

The preparation of e-keto-carboxylic acids and their derivatives has been the subject of a large number of investigations. According to Rodd, *The Chemistry of Carbon Compounds* (1952 edition), Vol. 1, pages 227-229, the following methods of preparation are available:
gentle oxidation of α-hydroxyacids containing a secondary hydroxyl group, or by the enzymatic deamination of α-amino-acids;
hydrolysis of an acyl cyanide;
hydrolysis of α-oximino-esters;
from glycidic acid esters on treatment with benzene saturated with boron trifluoride;
from α,β-dibromocarboxylic acids by forming a piperidine addition compound followed by hydrolysis;
from α-keto-acetals by ultraviolet irradiation in the presence of N-bromosuccinimide;
from α-bromomethylketones by boiling with selenium dioxide in absolute methanol or ethanol;
from carboxylic acid esters by oxidation with selenium dioxide;
permanganate oxidation of vinyl ketones;
from carboxylic acid esters by condensation with oxalic ester followed by decarboxylation;
from aldehydes via 5-alkylidene-2-thio-oxazolid-4-ones or by reaction with methyl methoxyacetate;
hydrolysis of azlactones or acetamido-acrylic acids;
hydrolysis of the reaction product of Grignard reagents on diethyl-oxamic ester;
oxidation of α-hydroxyacid esters containing two β-hydrogen atoms by N-bromosuccinimide in carbon tetrachloride to β-bromo-α-keto acid esters; and
by the action of alkali on the dimethanesulphonates and ditoluene-p-sulphonates of α,β-dihydroxycarboxylic acids.

Methods for preparing arylpyruvic acids also are known. For example, U.S. Pat. No. 4,152,352 discloses the preparation of an arylpyruvic acid by reacting an arylmethyl halide in a liquid solvent medium with carbon monoxide at pressures of 5 to 200 bars in the presence of a catalytic amount of a metal carbonyl compound and an alkaline earth metal inorganic base. Further, U.K. Patent Application No. 2,026,478A discloses that alkali metal salts of an arylpyruvic acid can be prepared by reacting an arylmethyl halide, carbon monoxide and an alkali metal base in the presence of a metal carbonyl compound as catalyst and in the presence of an alcohol or cyclic ether as solvent.

SUMMARY

It has now been found that alkyl α-keto-carboxylic acids of the general formula:

in which:
R represents a linear or branched alkyl radical having from 1 to about 20 carbon atoms can be prepared in high yields by carbonylating an alkyl halide of the general formula:

RX where R is as defined above and X represents halogen, in a liquid solvent medium, with carbon monoxide at a pressure of from about 300 to 3000 psig in the presence of a catalytic amount of a metal carbonyl compound and an alkali metal inorganic base or an alkaline earth metal inorganic base.

Alkyl halides suitable for use in the present process are linear or branched alkyl halides having from 1 to about 20 carbon atoms, although higher alkyl halides can be used, if desired. Alkyl-fluorides and alkyliodides may be used but it is preferable to use alkylhalides of the "middle halogens"—i.e., alkylchlorides and alkylbromides. Specific examples of preferred halides include the monochlorides and monobromides of methane, propane, butane, pentane, hexane, heptane, octane, nonone and other hydrocarbons having up to about 20 carbon atoms.

Methods for preparing alkyl halides are well known. For example, alkyl halides are formed when alcohols react with either inorganic acid halides or with hydrogen halides under appropriate reaction conditions. These two procedures are perhaps the most satisfactory general methods of preparation, although the addition of hydrogen halides to olefins and the direct halogenation of saturated hydrocarbons also may be used.

The reaction is carried out in the presence of a mixture of water and alcohol as a reaction medium in which the carbonylation of the alkyl halides takes place. Preferably, the alcohols employed for the reaction may be straight-chain, branched or cyclic, and preferably contain up to 6 carbon atoms. Methanol, ethanol, propanol, isopropanol, n-butanol, isobutanol, tertbutanol, and tert-amyl alcohol may be mentioned as examples. Cyclic ethers, such as tetrahydrofuran, also may be used. The particularly preferred solvent alcohol is tert-butanol. Mixtures containing about 10% to 90% by weight of water and about 90% to 10% by weight of alcohol generally are used. Preferred mixtures contain about 30% to 80% by weight water and about 70% to 20% by weight alcohol.

The reaction takes place in the presence of a basic substance suitably an alkali metal hydroxide or an alkaline earth metal hydroxide employing a metal carbonyl compound. Although not wishing to be bound by theory, it is believed that the alkyl halide compound undergoes a reaction with the carbon monoxide and basic substance whereby the salt of the alkyl α-keto-carboxylic acid is formed from which the keto-carboxylic acid is isolated after acidification in a known manner.

Specific examples of suitable basic agents which can be used in the practice of the process include: LiOH, NaOH, KOH, RbOH, Ca(OH)$_2$, Ba(OH)$_2$ and Mg(OH)$_2$. LiOH and Ca(OH)$_2$ are particularly preferred. Yields of alkyl α-keto-carboxylic acids of up to approximately 84% can be obtained using Ca(OH)$_2$ as the basic substance and a solvent medium of tert-butanol and water.

The amount of basic agent used can vary within wide limits. In general, the molar ratio of the alkali metal base or alkaline earth metal base to the alkyl halide is preferably 6:1 to 2:1.

In the process described herein, it is preferred to use metal carbonyl compounds as carbonylation catalysts. These catalysts include particularly metal carbonyls such as iron pentacarbonyl, dicobalt-octacarbonyl and nickel-tetracarbonyl, or their salts such as, for example, the potassium or sodium salts thereof. Dicobalt-octacarbonyl is very particularly suited. These catalysts can be added to the medium in the solid state or in the form of solutions in the solvent used for the carbonylation reaction. The weight ratio of the metal carbonyl compound to the alkyl halide is preferably from about 1:1 to 1:300 and more preferably from about 1:10 to 1:100.

Optionally, lithium iodide and/or bis(1,2-diphenylphosphino)ethane can be employed in the instant process as co-catalysts. Although experiments thus far have failed to define the exact role these two agents play in the overall process of the present invention, in some instances their presence appears to exert a yield enhancing effect on the reaction. For example, using lithium iodide and bis(1,2-diphenylphosphino)ethane as co-catalysts in the biscarbonylation of n-butyl bromide with lithium hydroxide as base and dicobalt-octacarbonyl as catalyst, a 62% yield of 2-oxohexanoic acid was obtained at 70°–80° C. and 800 psig CO pressure after four hours of reaction. The same reaction carried out for sixteen hours, however, in the absence of lithium iodide and bis(1,2-diphenylphosphino)ethane, only produced a 36% yield of 2-oxohexanoic acid. In contrast, however, an 83.7% yield of n-pentylpyruvic acid was obtained by the biscarbonylation of n-hexylbromide using calcium hydroxide as base, dicobalt-octacarbonyl as catalyst and no lithium iodide or bis(1,2-diphenylphosphino)ethane at reaction conditions similar to those aforedescribed. When used in the present process, only small amounts of from about 0.01 to 1 mole percent each of lithium iodide and bis(1,2-diphenylphosphino)ethane are employed.

The concentration of the alkyl halide used in the reaction solvent is not critical and can vary within wide limits. Thus, it can be between about 1 and 30% by weight, based on the weight of the solvent, however, it is possible to go outside of these limits without disadvantage.

The present process is advantageously carried out by bringing the mixture consisting of the alkyl halide, the metal carbonyl catalyst and the alkali metal base or alkaline earth metal base, suspended in the mixture of water and alcohol, into contact, under nitrogen, in a suitable pressure-resistant reactor equipped with a stirrer, with a large excess of carbon monoxide (amount greater than 2 moles of carbon monoxide per mole of the alkyl halide) introduced at the desired pressure and temperature, in accordance with techniques suitable for bringing about the reaction between a liquid phase and a gas phase.

The carbonylation reaction is carried out at a temperature in the range of from about 30° C. to about 150° C., preferably from about 50° C. to 100° C. over a period of time of from about 3 to 60 hours, typically 3 to 20 hours.

In general, the reaction takes place at elevated carbon monoxide pressures which may range from about 300 psig to about 3000 psig. Preferably, the reaction takes place at a pressure in the range of about 800 psig to 1000 psig. The carbon monoxide may contain or be mixed with an inert gas, such as nitrogen.

On completion of the reaction, the product mixture is filtered, resulting in the alkali metal salt or alkaline earth metal salt of the alkyl α-keto-carboxylic acid being separated from the liquid reaction components as the main solid component. The filtrate contains the remainder of the alkali metal salt or alkaline earth metal salt of the alkyl α-keto-carboxylic acid, and, where unbranched alcohols are used, also esters in addition to unreacted alkyl halide as well as acid and alcohol products fom the starting alkyl halide.

In a further process step, the metal salt of the alkyl α-keto-carboxylic acid is acidified with a dilute acid, such as hydrochloric acid, so as to displace the alkyl α-keto-carboxylic acid from its alkali metal salt or its alkaline earth metal salt. The solution obtained is extracted with a suitable solvent, for example, an ether such as diethyl ether, and the organic extract thus obtained is purified by conventional acid-base work-up. The final residue consists of very pure alkyl α-keto-carboxylic acid.

If desired, lower alkyl esters of the alkyl α-keto-carboxylic acid products of the present invention can be prepared by esterifying the alkyl α-keto-carboxylic acid product according to conventional esterification techniques employing lower aliphatic alkanol and acid catalysts, such as, for example, BF$_3$, BF$_3$.HCl, or BF$_3$.MeOH, BF$_3$.Et$_2$O or diazomethane at suitable reaction conditions.

Experiments have shown that certain reaction conditions and components give better yields of the desired salts and acids than others. Optimum yields range from about 50% to about 84%. The reaction appears most facile at CO pressures of approximately 800–1000 psig and at temperatures of from about 50° C. to 100° C. The chelating ability and size of the base cation, the stability and the solubility of the particular base in the solvent, temperature and CO pressure all appear to influence the reaction rate and product distribution.

The highest yield of alkyl u-keto-carboxylic acid which has been obtained thus far by the process of the invention is approximately 84%. This was obtained using Ca(OH)$_2$ in a tertiary butanol-water solvent medium at a reaction temperature of approximately 80° C. and a pressure between about 800 psig and about 900 psig. The starting reactant was n-hexylbromide and the keto-carboxylic acid product obtained was n-pentylpyruvic acid.

The following examples illustrate the invention.

EXAMPLE 1

6.8 g (50 mmoles) of n-butyl bromide, 700 mg (~2 mmoles) of Co$_2$(CO)$_8$, 6.0 g (150 mmoles) of NaOH, 30 ml t-BuOH, 80 ml of H$_2$O and 50 mg of bis(1,2-diphenylphosphino)ethane and 560 mg (3 mmoles) of LiI were stirred at 96° C. and under 800 psig CO pressure for 18 hours. The reaction mixture was cooled, acidified with excess HCl, and extracted with Et$_2$O to give a crude oily residue which was made basic with excess NaOH solution (checked with pH paper). The basic aqueous solution was washed with a little of $Et_2O$, experiments using varying conditions of reaction and different reactants are given in the following table.

TABLE

Preparation of Alkyl α-Keto-Carboxylic Acid by Reaction of Alkyl Halide With Carbon Monoxide in the Presence of Metal Carbonyl, Base and Solvent

| Example No. | Base/ mmoles/ | Solvent ml | $Co_2(CO)_8$ (mmoles) | CO (psig) | Temp. (0° C.) | Time (hours) | | | |
|---|---|---|---|---|---|---|---|---|---|
| | n-$C_4H_9BR$ (mmoles) | | | | | | $R_4COCO_2H$ % Yield | $R_5CO_2H$ % Yield | $R_4OH$ % Yield |
| 4 | 50 | LiOH (200) | t-BuOH (30) $H_2O$ (80) | ~2 | 900 | 90 | 16 | 36 | 27 | N/A |
| 5[1] | 50 | $Ca(OH)_2$ (130) | t-BuOH (30) $H_2O$ (80) | ~2 | 900 | 90 | 15 | 56 | N/A | N/A |
| | n-$C_6H_{13}BR$ (mmoles) | | | | | | $R_6COCO_2H$ % Yield | $R_7CO_2H$ % Yield | $R_6OH$ % Yield |
| 6 | 50 | $Ca(OH)_2$ (100) | t-BuOH (30) $H_2O$ (70) | ~2 | 850–970 | 80 | 22.5 | 80.6 | 3.8 | 1.6 |
| 7 | 50 | $Ca(OH)_2$ (100) | t-BuOH (30) $H_2O$ (70) | ~2 | 850–980 | 120 | 23 | 62.8 | 23.5 | 2.1 |
| 8 | 50 | $Ca(OH)_2$ (55) | t-BuOH (30) $H_2O$ (70) | ~2 | 850–950 | 80 | 22.5 | 54.9 | 35.3 | 1.3 |
| 9 | 50 | LiOH | t-BuOH (30) $H_2O$ (70) | ~2 | 850–860 | 77 | 18 | 62.8 | 30.6 | 0 |
| 10 | 50 | LiOH (200) | t-BuOH (30) $H_2O$ (70) | ~2 | 850–870 | 60 | 20 | 0[2] | 0 | 0 |
| 11 | 50 | LiOH (200) | t-BuOH (30) $H_2O$ (70) | ~2 | 820 | 60 | 16 | 74.5 | 15.1 | 0 |
| 12 | 50 | $Ca(OH)_2$ (100) | t-BuOH (70) $H_2O$ (30) | ~2 | 840–980 | 80 | 17 | 83.7 | 8.2 | trace |
| 13 | 50 | $Ca(OH)_2$ (100) | i-propyl (30) $H_2O$ (70) | ~2 | 820–860 | 80 | 16 | 0[3] | 0 | 0 |
| 14 | 50 | $Ca(OH)_2$ (100) | i-propyl (30) $H_2O$ (70) | ~2 | 850–970 | 80 | 17 | 45.0 | 24.2 | 9.7 |
| 15 | 50 | $Ca(OH)_2$ (100) | THF (30) $H_2O$ (70) | ~2 | 850–970 | 80 | 17 | 68.2 | 18.0 | 2.7 |
| | n-$C_{12}H_{25}BR$ (mmoles) | | | | | | $R_{12}COCO_2H$ % Yield | $R_{13}CO_2H$ % Yield | $R_{12}OH$ % Yield |
| 16 | 50 | LiOH (200) | t-BuOH (30) $H_2O$ (70) | ~2 | 900 | 70 | 16 | 35 | 23 | 30 |

[1] 0.1 mmole bis(1,2-dihenylphosphino)ethane present
[2] reactor contents spilled
[3] reactor contents spilled acidified with HCl (checked with pH paper), and extracted again with $Et_2O$ to give 70% of a mixture of acids. $^1H$ NMR showed it contained 50% of valeric acid and 20% of 2-oxohexanoic acid. $^{13}C$ NMR confirmed these structural assignments.

EXAMPLE 2

6.8 g (50 mmoles) of n-butyl bromide, 4.8 g (200 mmoles) of LiOH, 30 ml of t-BuOH, 80 ml of $H_2O$, ~700 mg (~2 mmoles) of $Co_2(CO)_8$, 560 mg (~3 mmoles) of LiI, and 56 mg (0.1 mmole) of bis(1,2-diphenylphosphino)ethane were stirred in a 300 ml autoclave at 70°–80° C. under 800 psig CO pressure for 4 hours. Similar workup as in Example 1 gave a 62.2% yield of 2-oxo-hexanoic acid and an 8% yield of valeric acid based on $^1H$ NMR spectrum of the mixture.

EXAMPLE 3

6.8 g (50 mmoles) of n-butyl bromide, 7.4 g (100 mmoles) of $Ca(OH)_2$, ~700 mg (~2 mmoles) of $Co_8(CO)_8$, 560 mg (~3 mmoles) of LiI, 50 mg (0.1 mmole) of bis(1,2-diphenylphosphino)ethane, 30 ml of t-BuOH, and 80 ml of $H_2O$ were stirred at 90° C. and under 800 psig CO pressure for 18 hours. The reaction mixture was cooled at room temperature and filtered; the crude cake was rinsed with a little of $Et_2O$, acidified with excess HCl (checked with pH paper) and extracted with $Et_2O$ to give a 50.2% isolated yield of 2-oxohexanoic acid.

In a similar manner, several other examples of the present invention were carried out. The results of such

EXAMPLE 17

15.1 g (100 mmoles) of 3-methyl-1-bromobutane, 1.71 g (5 mmoles) of $Co_2(CO)_8$, and 22.23 g (300 mmoles) of $Ca(OH)_2$, were combined in a 150 mLs deoxygenated 70% t-butanol/30% water under a stream of CO in an autoclave. The autoclave was sealed and pressurized to 860 psi with carbon monoxide and heated to 90° C. for 9 hours. The autoclave was vented and the solid product isolated by filtration through a coarse frit. The crude calcium salt was transferred to a 500 mL flask and acidified with cooling. The resultant aqueous solution was extracted with diethyl ether (3×70 mLs), combined, dried over $MgSO_4$ and evaporated to give 4.36 g (33%) of 2-oxo-5-methylhexanoic acid.

Having described the process which Applicant regards as his invention, it should be recognized that changes and variations within the scope and spirit of the invention can be made by one skilled in the art and it is accordingly to be understood that the present description of the invention is illustrative only. It is desired that the invention be limited only by the lawful scope of the following claims.

I claim:

1. A process for the production of an alkyl alpha-keto-carboxylic acid of the general formula:

RCOCOOH or a salt thereof wherein: R is a linear or branched alkyl radical having from 1 to about 20 carbon atoms which comprises reacting an alkyl halide of the formula:

RX where R is as defined above and X represents halogen in a liquid solvent medium, with carbon monoxide at a temperature in the range of from about 30° C. to about 150° C. and elevated pressure of about 300 psig to 3,000 psig in the presence of a catalytic amount of a metal carbonyl compound, a cocatalyst selected from the group consisting of lithium iodide and bis(1,2-diphenylphosphino) ethane, and an alkali metal inorganic base to form a salt of the alpha-keto-carboxylic acid, and then optically acidifying the salt to form said acid.

2. A process of claim 1 wherein said cocatalyst is lithium iodide.

3. A process according to claim 2, wherein the amount of lithium iodide present in said reaction is from about 0.01 to about 1 mole percent.

4. A process of claim 1 wherein said co-catalyst is bis(1,2-diphenylphosphino)ethane.

5. A process according to claim 4, wherein the amount of bis(1,2-diphenylphosphino)ethane present in said reaction is from about 0.01 to about 1 mole percent.

* * * * *

UNITED STATES PATENT AND TRADEMARK OFFICE
CERTIFICATE OF CORRECTION

PATENT NO.  :  4,738,802
DATED       :  April 19, 1988
INVENTOR(S) :  John Y. Lee It is certified that error appears in the above-identified patent and that said Letters Patent is hereby corrected as shown below:

Column 1, line 22, reads "e-keto-carboxylic" and should read -- α-keto-carboxylic --.

Column 4, line 36, reads "$BF_3.HCl$" and should read -- $BF_3 \cdot HCl$ --.

Column 4, line 37, reads "$BF_3.MeOH, BF_3.Et_2O$" and should read -- $BF_3 \cdot MeOH, BF_3 \cdot Et_2O$ --.

Column 4, line 49, reads "u-keto-carboxylic" and should read -- α-keto-carboxylic --.

Signed and Sealed this

Sixth Day of September, 1988

Attest:

DONALD J. QUIGG

*Attesting Officer*     *Commissioner of Patents and Trademarks*